(12) United States Patent
Mason

(10) Patent No.: US 7,129,265 B2
(45) Date of Patent: Oct. 31, 2006

(54) SYNERGISTIC EFFECTS OF AMLODIPINE AND ATORVASTATIN METABOLITE AS A BASIS FOR COMBINATION THERAPY

(76) Inventor: R. Preston Mason, P.O. Box 418, Manchester, MA (US) 01944

(*) Notice: Subject to any disclaimer, the term of this patent is extended or adjusted under 35 U.S.C. 154(b) by 0 days.

(21) Appl. No.: 10/033,149

(22) Filed: Oct. 19, 2001

(65) Prior Publication Data

US 2002/0086889 A1    Jul. 4, 2002

Related U.S. Application Data

(63) Continuation-in-part of application No. 09/556,930, filed on Apr. 21, 2000, now abandoned.

(60) Provisional application No. 60/166,592, filed on Nov. 19, 1999, provisional application No. 60/151,121, filed on Aug. 27, 1999, provisional application No. 60/145,305, filed on Jul. 23, 1999, provisional application No. 60/130,665, filed on Apr. 23, 1999.

(51) Int. Cl.
*A61K 31/40* (2006.01)

(52) U.S. Cl. .................................................. 514/422

(58) Field of Classification Search ................ 514/423, 514/356, 427, 277, 408, 422
See application file for complete search history.

(56) References Cited

U.S. PATENT DOCUMENTS 4,879,303 A * 11/1989 Davison et al.
5,385,929 A * 1/1995 Bjorge et al.
6,455,574 B1 * 9/2002 Buch ........................... 514/427

FOREIGN PATENT DOCUMENTS

| WO | WO95/05822 | * | 3/1995 |
| WO | WO 99/11259 |  | 3/1999 |

OTHER PUBLICATIONS

Jukema et al., Evidence for a synergistic effect of CCBs with lipid-lowering therapy in retarding progression of coronary atherosclerosis in symptomatic patients with normal to moderately raised cholesterol level., abstractPMID: 8630669, (1996).*
The Merck Index, Therapeutic Category and Biological Index p. THER-10-11, 12th Edition, 1996.*
Hardman et al. "Goodman & Gilman's The Pharmacological Basis of Therapeutics" (9th ed, 1996) p. 51 and 57-58.*
Pfizer News, May 20, 1997, p. 1-5.*

(Continued)

*Primary Examiner*—San-ming Hui
(74) *Attorney, Agent, or Firm*—Burns & Levinson LLP; Stephen J. Gaudet; Janine M. Susan

(57) ABSTRACT

The combination of amlodipine with atorvastatin metabolite shows a synergistic antioxidant effect on lipid peroxidation in human low-density lipoproteins and membrane vesicles enriched with polyunsaturated fatty acids. Inhibition of oxy-radical damage by this drug combination was observed at therapeutic levels in a manner that could not be reproduced by the combination of amlodipine with other statins or the natural antioxidant, vitamin E. The basis for this potent activity is attributed to the chemical structures of these compounds and their molecular interactions with phospholipid molecules, as determined by x-ray diffraction analyses. This combination therapy can be used to treat cardiovascular disorders, especially coronary artery disease, by increasing the resistance of low-density lipoproteins and vascular cell membranes against oxidative modification.

11 Claims, 13 Drawing Sheets

OTHER PUBLICATIONS

"Norvasc", FDA approval Feb. 7, 1995.*
Gilligan et al. Journal of the American College of Cardiology, (Dec 1994) 24 (7) 1611-17.*
Bertram Pitt, MD et al. Effect of Amlodipine on the Progression of Atherosclerosis and the Occurrence of Clinical Events, pp. 1503-1510, Sep. 26, 2000.
Glenn N. Levine, MD et al. Cholesterol Reduction in Cardiovascular Disease, The New England Journal of Medicine, pp. 512-521, Feb. 23, 1995.
Seymour Glagov, MD et al., Compensatory Enlargement of Human Atherosclerotic Coronary Arteries, The New England Journal of Medicine, vol. 316, No. 22, pp. 1371-1371.

* cited by examiner

Computed Enthalpies of Formation for
Atorvastatin Metabolite Radicals *

| Molecule | $\Delta H_f$ (kcal/mol) |
|---|---|
| Carbon radical | −209.50 |
| Oxygen radical | −199.89 |
| Nitrogen radical | −192.55 |
| Methyl radical | −193.51 |
| Phenyl radical | −176.05 |
| Carbon/Oxygen Diradical | −182.07 |
| Carbon/Nitrogen Diradical | −174.25 |

*The smaller (i.e., more negative) the $\Delta H_f$ value, the easier to abstract the H atom from that site.

Computed Enthalpies of Formation for
Amlodipine Radicals*

| Molecule | $\Delta H_f$ (kcal/mol) |
|---|---|
| Carbon radical | −164.28 |
| Nitrogen radical | −148.27 |

*The smaller (i.e., more negative) the $\Delta H_f$ value, the easier to abstract the H atom from that site.

FIG. 7

SYNERGISTIC EFFECTS OF AMLODIPINE AND ATORVASTATIN METABOLITE AS A BASIS FOR COMBINATION THERAPY

CROSS REFERENCE TO RELATED APPLICATIONS

This application claims priority from the following four provisional patent applications: U.S. application No. 60/130,665, filed on Apr. 23, 1999; U.S. application No. 60/145,305, filed on Jul. 23, 1999; U.S. application No. 60/151,121, filed on Aug. 27, 1999; and U.S. application No. 60/166,592, filed on Nov. 19, 1999, and is a continuation-in-part application of our U.S. application Ser. No. 09/556,930 filed Apr. 21, 2000 now abandoned.

FIELD OF INVENTION

The present invention relates to pharmaceutical compositions and combinations to treat arterial and related heart disease and related ailments.

BACKGROUND OF INVENTION

Coronary artery disease (CAD) is the leading cause of mortality in the developed world, and is associated with substantial morbidity as well. Typically, the patient with CAD has several concomitant conditions, including hypertension, diabetes, and dyslipidemia, increasing overall risk for poor outcomes and complicating treatment.

Among antihypertensive therapies, the lipophilic dihydropyridine-type calcium channel blocker CCB) amlodipine besylate (AML) is a very well-tolerated agent with an established record of safety and effectiveness for the treatment of hypertension and angina. A potential therapeutic role for AML in the treatment of patients with CAD was recently shown in the Prospective Randomized Evaluation of the Vascular Effects of Norvasc® (AML) Trial (PREVENT). This three-year trial evaluated the effects of AML compared to placebo on the development and progression of atherosclerotic lesions in coronary and carotid arteries among patients with documented CAD (Byington R P, Miller M E, Herrington D, et al. Rationale, design, and baseline characteristics of the Prospective Randomized Evaluation of the Vascular Effects of Norvasc Trial (PREVENT). Am. J. Cardiol. 1997; 80:1087–1090). The results of PREVENT showed impressive clinical benefits with AML therapy, including an overall 30% reduction in major documented events or procedures (Byington R P, Chen J, Furberg C D, Pitt B. Effect of amlodipine on cardiovascular events and procedures. J. Am. Coll. Cardiol. 1999; 33:314A and Pitt B, Byington R P, Hunninghake D B, Mancini J, Miller M E, Riley W. Effect of amlodipine on the progression of atherosclerosis and occurrence of clinical events. Circulation 2000; 102:1503–1510). AML therapy was also associated with a significant slowing in the progression of carotid atherosclerosis, as measured by B-mode ultrasonographic assessments (Byingyton R, Riley W, Booth D, et al. Effect of amlodipine on progression of carotid atherosclerosis in patients with documented heart disease. Am. J Hypertens. 1999; 12:42A–43A and Pitt B, Byington R P, Hunninghake D B, Mancini J, Miller M E, Riley W. Effect of amlodipine on the progression of atherosclerosis and occurrence of clinical events. Circulation 2000; 102:1503–1510). The clinical benefit seen with AML in CAD has not been previously reported with other CCBs, including dihydropyridine-type agents that have been used to examine this question (Waters D, Lesperance J, Francetich M, et al. A controlled clinical trial to assess the effect of a calcium channel blocker on the progression of coronary atherosclerosis. Circulation 1990; 82:1940–1953; Lichtlen P R, Hugenholtz P G, Rafflenbeul W, et al. Retardation of coronary artery disease in humans by the calcium-channel blocker nifedipine: Results of the INTACT study (International Nifedipine Trial on Antiatherosclerotic Therapy). Cardiovasc. Drugs Ther. 1990; 4:S1047–S1068; Borhani N O, Mercuri M. Borhani P A, et al. Final outcome results of the Multicenter Isradipine Diuretic Atherosclerosis Study (MIDAS). A randomized controlled trial. JAMA 1996; 276: 785–791). This observation has led to interest in potential antiatherogenic properties of AML, including antioxidant effects that are independent of calcium channel modulation (Mason R P, Leeds P R, Jacob R E, et al. Inhibition of excessive neuronal apoptosis by the calcium antagonist amlodipine and antioxidants in cerebellar granule cells. J. Neurochem. 1999; 72:-1448–1456; Tulenko T N, Laury-Kleintop L, Walter M F, Mason R P. Cholesterol, calcium and atherosclerosis: Is there a role for calcium channel blockers in atheroprotection? Int. J. Cardiol. 1997; 62 (2 Suppl):55S–66S; Kramsch D M, Sharma R C. Limits of lipid-lowering therapy: The benefits of amlodipine as an anti-atherosclerotic agent. J Hum. Hypertens. 1995; 9 (Suppl 1:S3–S9); and Mason R P, Walter M F, Trumbore M W, Olmstead E G, Mason P E. Membrane antioxidant effects of the charged dihydropyridine calcium antagonist amlodipine. J. Mol. Cell. Cardiol 1999; 1:275–281.

Hypolipidemic therapy has also been demonstrated to be very useful in reducing morbidity and mortality associated with CAD. The ortho- and para-hydroxylated metabolites of atorvastatin ATM have been shown to exhibit antioxidant effects in lipoprotein preparations (Aviram M, Rosenblat M, Bisgaier C L, Newton R S. Atorvastatin and gemfibrozil metabolites but not the parent drugs, are potent antioxidants against lipoprotein oxidation. Atherosclerosis 1998: 138: 271–280). The ortho-, meta-, and para-hydroxylated metabolites of atorvastatin (ATM) and their methods of preparation are shown in U.S. Pat. No. 5,385,929.

However, no pharmaceutical composition currently exists that treats both hypertension and hyperlipidemia. Such a pharmaceutical composition would have several benefits. For example, the multiple risk factors for arterial and related heart disease that are often present in an individual patient could be targeted simultaneously. Additionally, the ease of taking one combined dosage could significantly enhance patient compliance with therapeutic regimens.

Therefore, it is an object of this invention to provide a combination therapy that will treat the multiple pathological processes involved in arterial and related heart disease.

These include, but are not limited to, hypertension and hyperlipidemia. It is also an object of is invention to develop useful and convenient dosage levels and forms of such a combination therapeutic. Preferably, this pharmaceutical composition would have synergistic effects on these hallmarks of arterial and related heart disease, such that the individual effects of the components of this composition would be enhanced by their combination.

Thus, this invention encompasses a therapeutic goal for the treatment of CAD that entails the development of drugs that can simultaneously target multiple underlying disease processes that contribute to atherosclerosis, thereby altering the course of the disease. Therefore, using this invention, CAD therapy may have increased positive outcomes if the use of an antihypertensive agent and HMG-CoA reductase inhibitor was combined in a single delivery system.

SUMMARY OF THE INVENTION

Unexpectedly, when AML and ATM were combined, they had a synergistic effect in preventing lipid peroxidation in human low-density lipoproteins (LDL) and lipid membranes. The activity of the combination is considered synergistic as the measured effect significantly exceeded any additive effects of the two drugs. Therefore, these agents have heretofore unrecognized synergistic antioxidant effects, a property that would enable these agents to increase the resistance of LDL and vascular cell membranes to oxidative modification during atherogenesis. Indeed, oxidative modification of lipids is a well-established cause of injury to the endothelium and underlying smooth muscle (Ross R. Atherosclerosis—An inflammatory disease. *N. Engl. J. Med.* 1999; 340:115–126; Diaz M N, Frei B, Vita J A, Keaney J F. Antioxidants and atherosclerotic heart disease. *N. Engl. J. Med.* 1997; 337:408–416). Lipophilic agents that protect against lipid peroxidation have been shown to reduce lesion development in various models of atherosclerosis as well as clinical studies (Diaz M N, Frei B, Vita J A, Keaney J F. Antioxidants and atherosclerotic heart disease. *N. Engl. J. Med.* 1997; 337:408–416). Moreover, the benefit associated with hypolipidemic therapy is attributed to both its effect on plasma very low-density lipoproteins (VLDL), LDL, and high-density lipoproteins (HDL) levels and, as a consequence, to a reduction in the potential formation of atherogenic oxidized lipoproteins. Scientific analyses that support the combined use of AML (Norvasc®) and ATM in a single delivery system for the treatment of cardiovascular disease are described in this invention. Specifically, the synergistic antioxidant activities of the calcium channel blocker, AML, and the active hydroxylated metabolite of the HMG-CoA reductase inhibitor atorvastatin, ATM were evaluated in human LDL and lipid membranes enriched with polyunsaturated fatty acids (PUFA), the key target for oxy-radical damage in atherosclerosis. The synergistic effects of these agents were demonstrated in membranes prepared in the presence of cholesterol. The combination of AML with ATM effected a dramatic and sustained reduction in lipid oxy-radical damage at concentrations as low as 10.0 nM. The dose-dependent antioxidant activity associated with the combination of these drugs at therapeutic levels was highly synergistic and could not be effectively reproduced by the endogenous agent, vitamin E. Antioxidant activity was not observed, however, when AML was combined with other HMG-CoA reductase inhibitors, including lovastatin and mevastatin. As determined by x-ray diffraction and chemical analyses, the distinct activity described for this drug combination can be attributed to strong physico-chemical interactions with the membrane bilayer that are independent of the well-characterized effects of these drugs on calcium transport and cholesterol metabolism. This synergistic antioxidant benefit constitutes a new pharmacologic mechanism of action for these compounds and a compelling rationale for the combined use of the active ingredients in Norvasc® and ATM in the treatment of cardiovascular disease by reducing the levels of LDL in plasma and improving protection of LDL and cellular membranes against oxidation. This new property complements the established effects of these drugs on hypertension and dyslipidemia. Other objects, features, and advantages of the present invention will be apparent from the following Detailed Description of the Preferred Embodiments taken in conjunction with the accompanying drawings in which:

BRIEF DESCRIPTION OF THE DRAWINGS

FIG. 7 shows the computed enthalpies for ATM, AML and their respective radical species.

In FIG. 8A, AML is the dotted line; in FIG. 8B, ATM is the dotted line; in FIG. 8C, the combination of AML and ATM is the dotted line. The darkened areas in each panel are the difference in electron densities between the control and treatment electron density profiles.

DETAILED DESCRIPTION OF EMBODIMENTS

Figure 1:
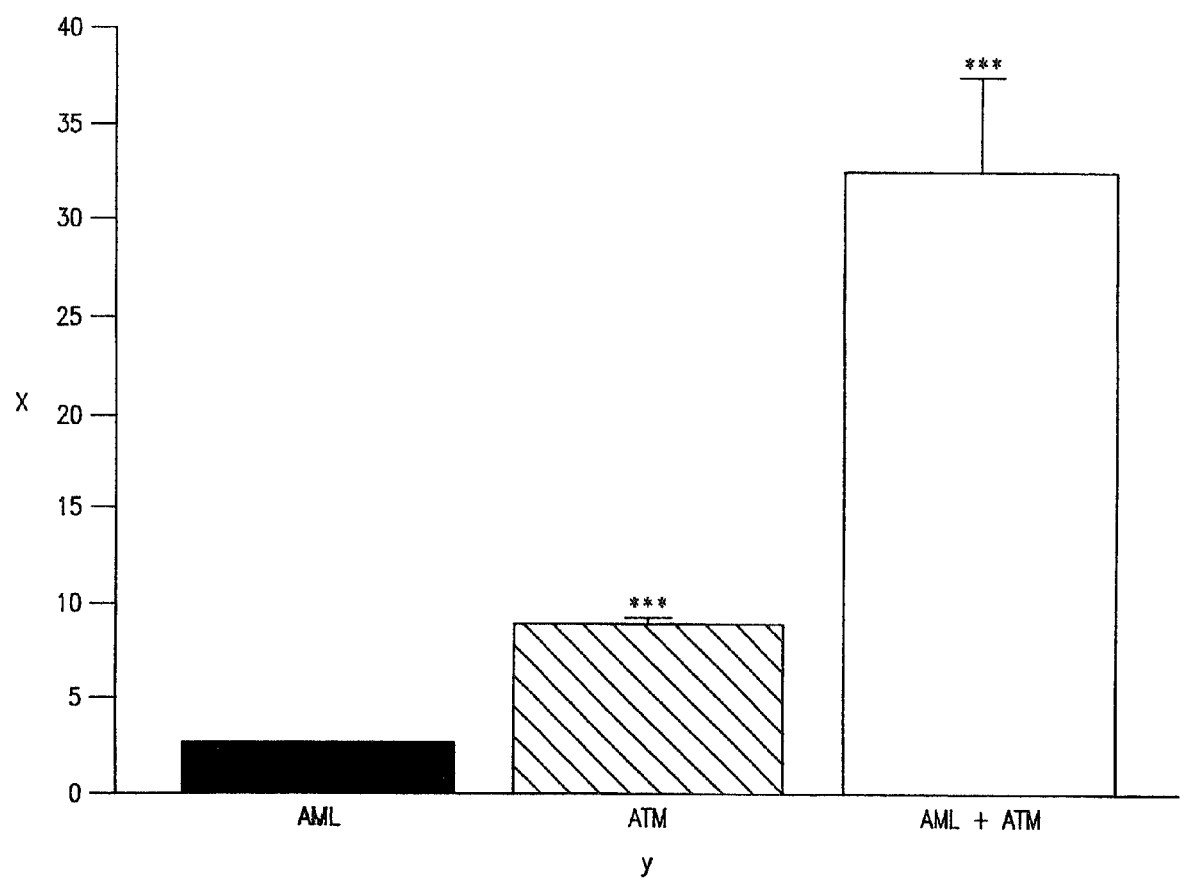
FIG. 1 shows the synergistic effects of AML and ATM on lipid peroxidation at a low, therapeutic concentration of drug (100.0 nM) in membranes containing physiologic levels of cholesterol. x is percent inhibition of lipid peroxidation and y is treatment with amlodipine (AML), atorvastatin metabolite (ATM), and the combination of both (AML+ATM) at a level of 100 nM. Values are mean±standard deviation for n 6 . . . indicates $p<0.001$ versus control and other treatments.
Figure 2:
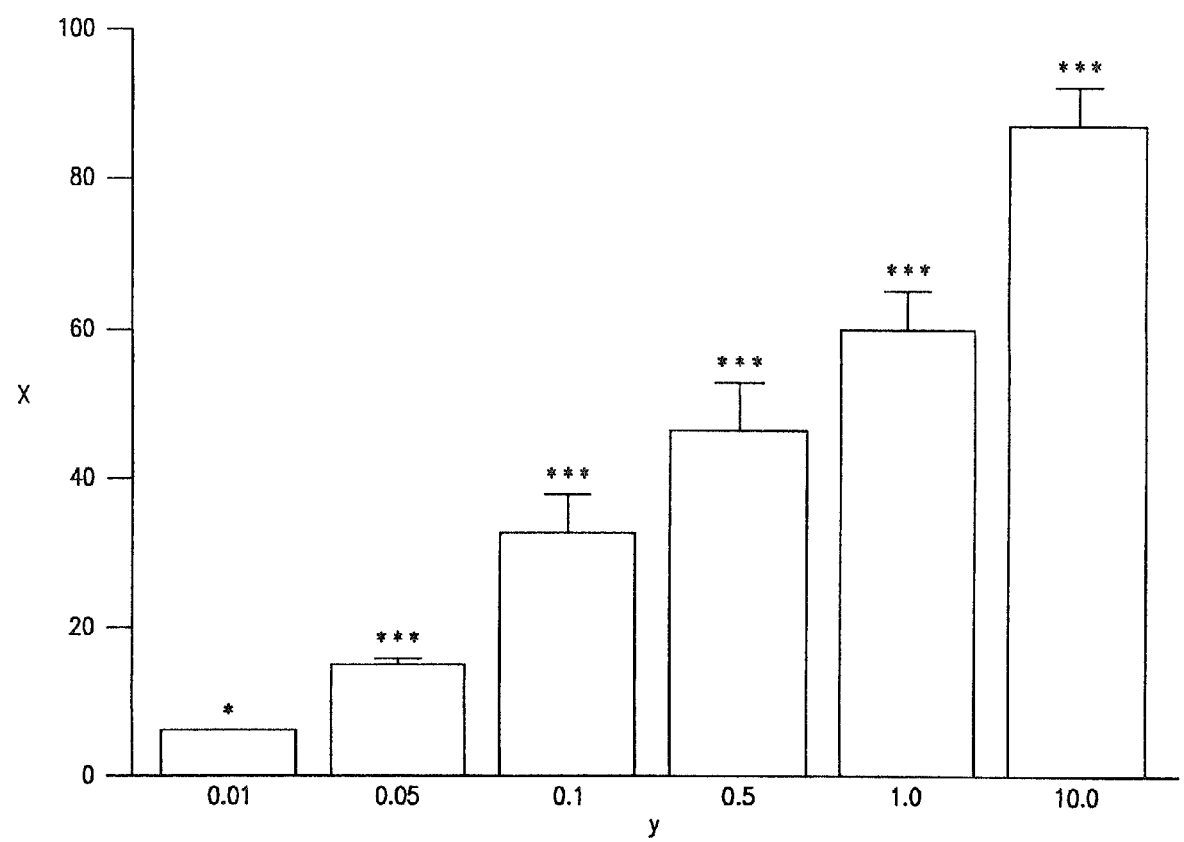
FIG. 2 shows the dose-dependent antioxidant effect of the combination of AML and ATM over a broad range of concentrations (0.01 through 10.0 μM). x is percent inhibition of lipid peroxidation and y is treatment with the combination of AML and ATM at the micromolar concentrations indicated. Values are mean±standard deviation for n=6. *** indicates $p<0.001$ versus control and other treatments.

Synergistic Antioxidant Effects of Amlodipine with Atorvastatin Metabolite in Lipid Membranes:

The separate and combined dose-dependent antioxidant activities of AML, and ATM were tested in membrane vesicles reconstituted from phospholipids enriched with cholesterol and the PUFA, dilinoleoyl phosphatidylcholine, at a 0.5:1 mole ratio. Membrane vesicles were used in these experiments for the following reasons: 1) this system is well-defined and highly reproducible; 2) linoleic acid represents the primary target for oxidative damage and is common in vascular cell membranes and lipoprotein particles; 3) this membrane system does not contain calcium channels or the HMG CoA reductase enzyme and; 4) lipid peroxidation in this system can be initiated spontaneously at 37° C. in the absence of exogenous chemical initiators, such as high levels of iron and ascorbate. In these experiments, oxidation occurred in a gradual, time-dependent manner that was measured spectrophotometrically over a 72 h period. In FIG. 1, the synergistic antioxidant activity of AML and ATM was demonstrated in membrane vesicles composed of cholesterol and phospholipid at levels that reproduce physiologic-like conditions (Tulenko T N, Chen M, Mason P E, Mason R P. Physical effects of cholesterol on arterial smooth muscle membranes: Evidence of immiscible cholesterol domains and alterations in bilayer width during atherogenesis. *J. Lipid. Res.* 1998; 39:947–956). At 100.0 nM, only the ATM separately produced any significant inhibition (9% of control) of lipid peroxidation in this membrane preparation enriched with cholesterol. When the agents were combined, however, the extent of inhibition increased to 33%, an effect significantly (p<0.01) greater than that measured for the agents separately. The antioxidant activity of the combination was very apparent: the drugs inhibited lipid peroxide formation (>5×10$^2$ µM) at a concentration of 100.0 nM (the control level of lipid peroxide formation was 1.6 mM). This drug combination produced an effect that was highly dose-dependent over a broad range of concentrations (FIG. 2). Significant inhibition (p<0.05) was observed as low as 10.0 nM with an IC$_{50}$ of 500.0 µM. Greater than 90% inhibition (>1 mM lipid peroxide formation) was observed at a concentration of 10.0 µM for the combination (FIG. 2). The fact that inhibition was observed at submicromolar levels indicates that the benefit observed with the combination of AML and ATM is of therapeutic relevance.

Figure 3:
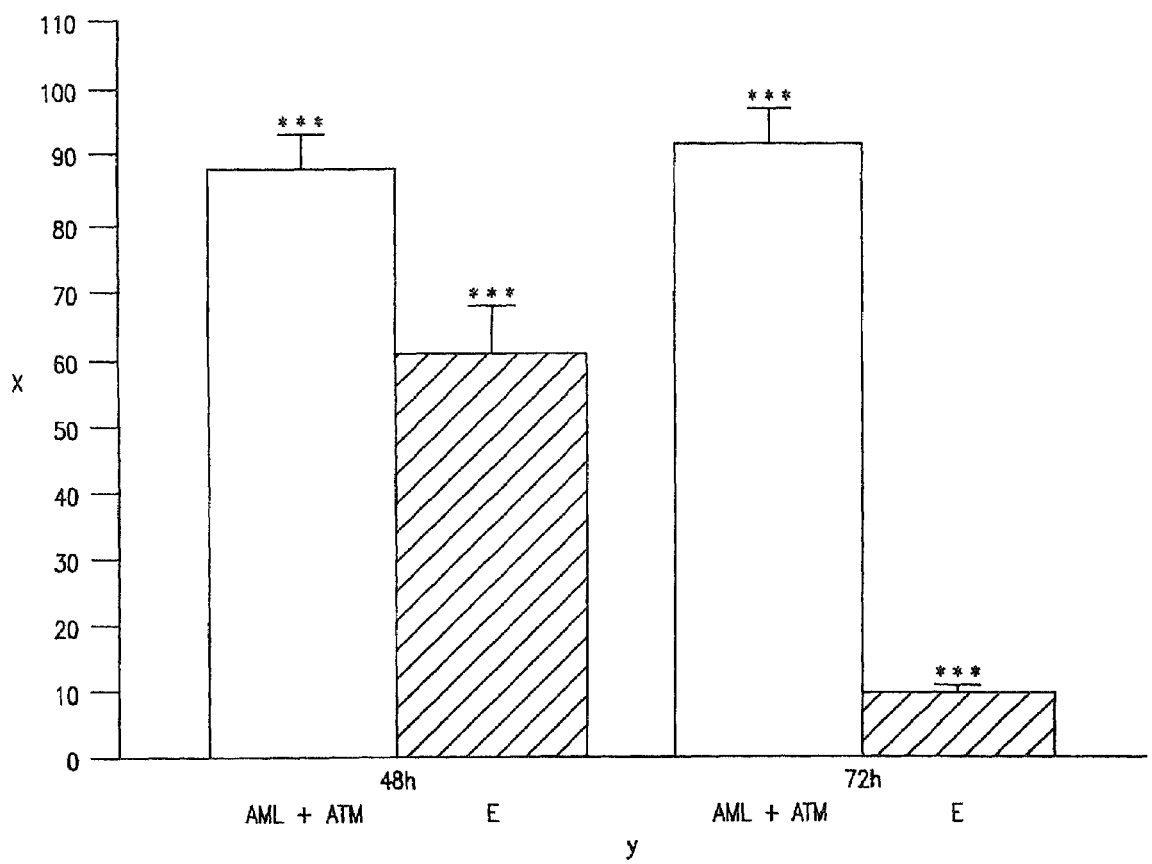
FIG. 3 shows the superior antioxidant activity of the AML/ATM combination over vitamin E as a function of time at an identical concentration (10.0 μM). x is percent inhibition of lipid peroxidation and y is treatment with the combination of amlodipine and atorvastatin metabolite (AML+ATM), darkened panel, or vitamin E (E), cross-hatched panel, both at 10 μM. Values are mean±standard deviation for n=6 to 12. *** indicates $p<0.001$ versus control and other treatments.
Figure 4A:
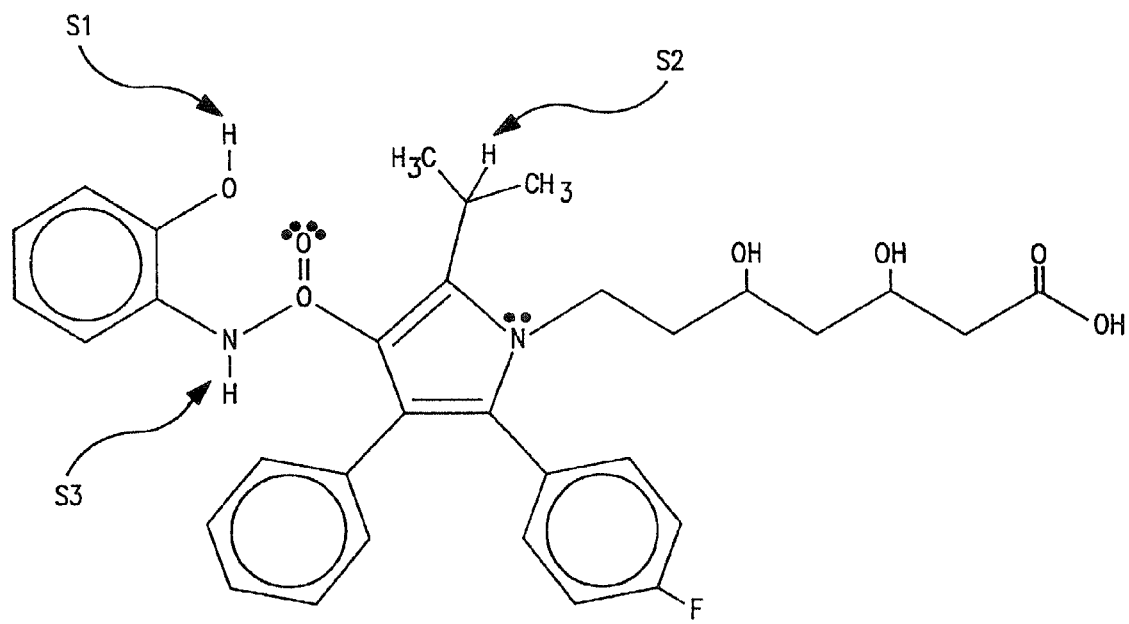
FIGS. 4A–4D show the sites of proton abstraction (S1, S2, and S3) for ATM that contribute to antioxidant activity in FIG. 4A along with resonance stabilization calculations (FIGS. 4B through 4D).
Figure 4B:
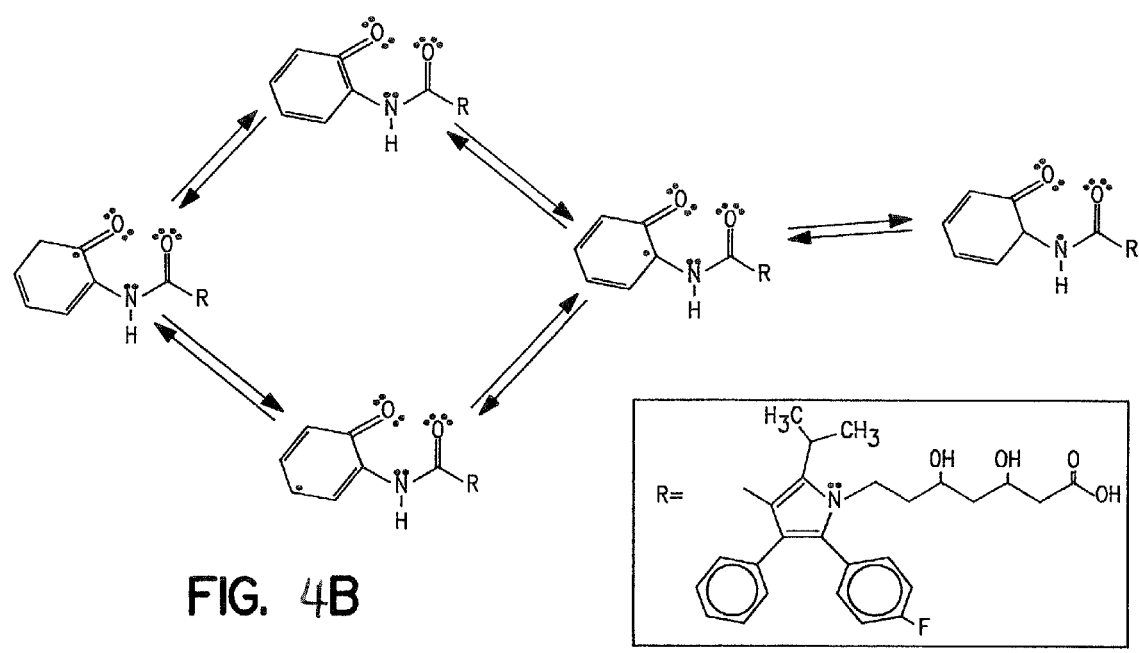
Figure 4C:
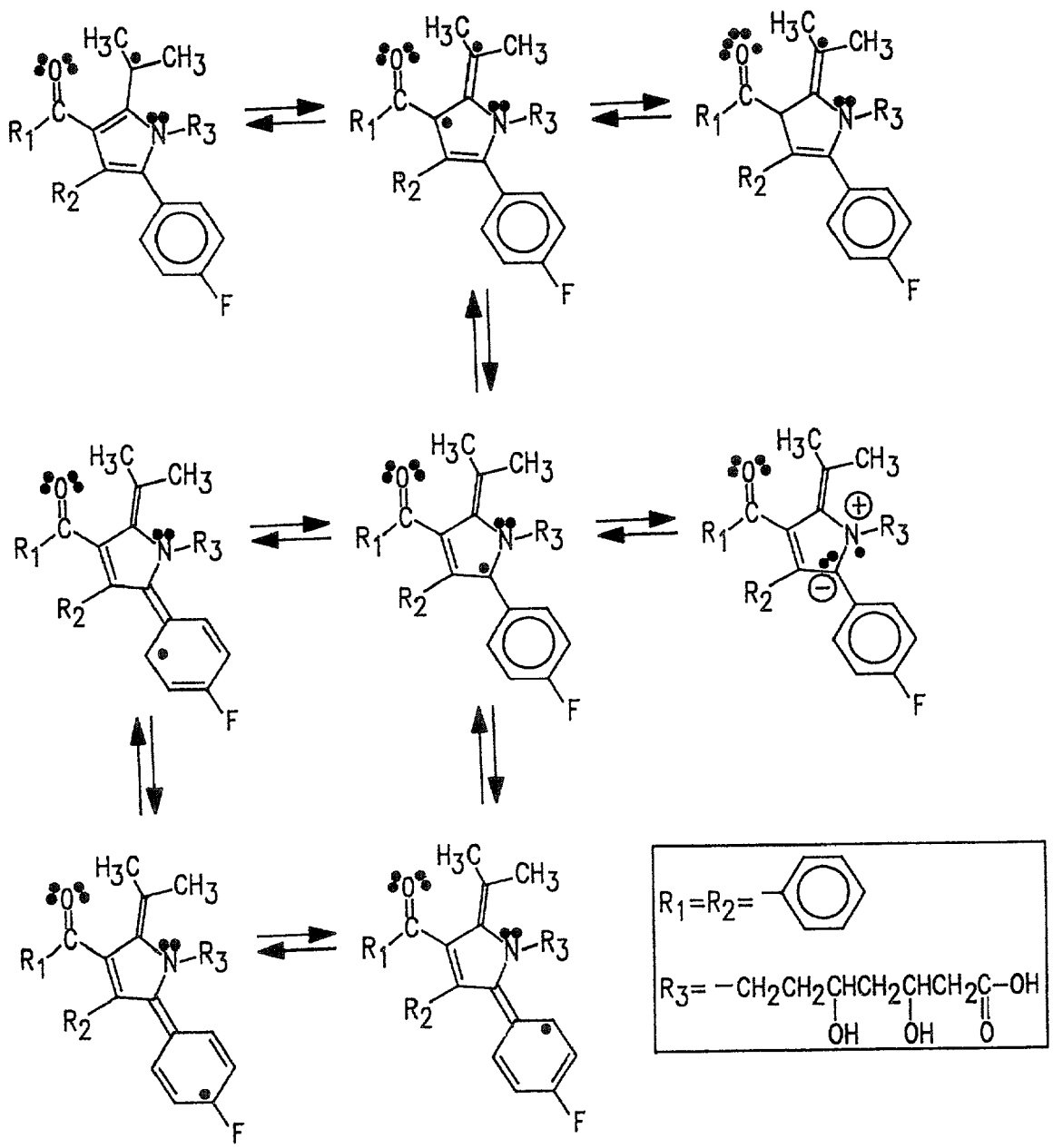
Figure 4D:
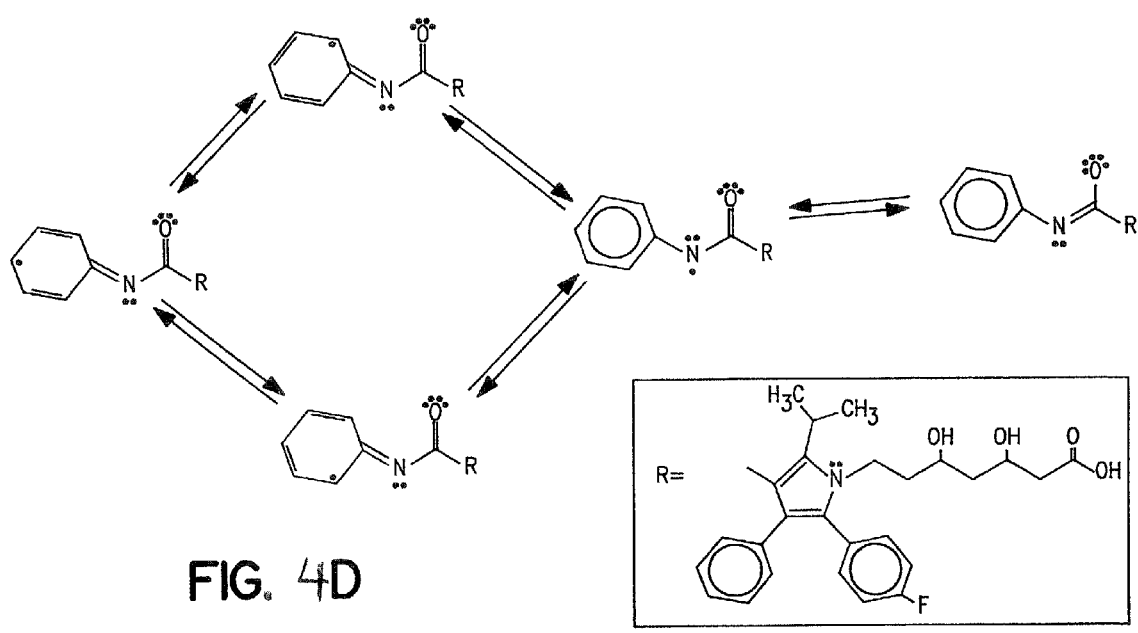

The antioxidant effect of the combination persisted over time in a manner that could not be reproduced by vitamin E, even at an elevated concentration (10.0 µM) (FIG. 3). This observation is consistent with the concept that vitamin E or α-tocopherol is gradually consumed during the lipid peroxidation process. By contrast, the activity of the AML/ATM combination was not affected by the length of the incubation period in which the total lipid peroxide level increased to 2.2 mM at the 72 h time point.

Figure 5:
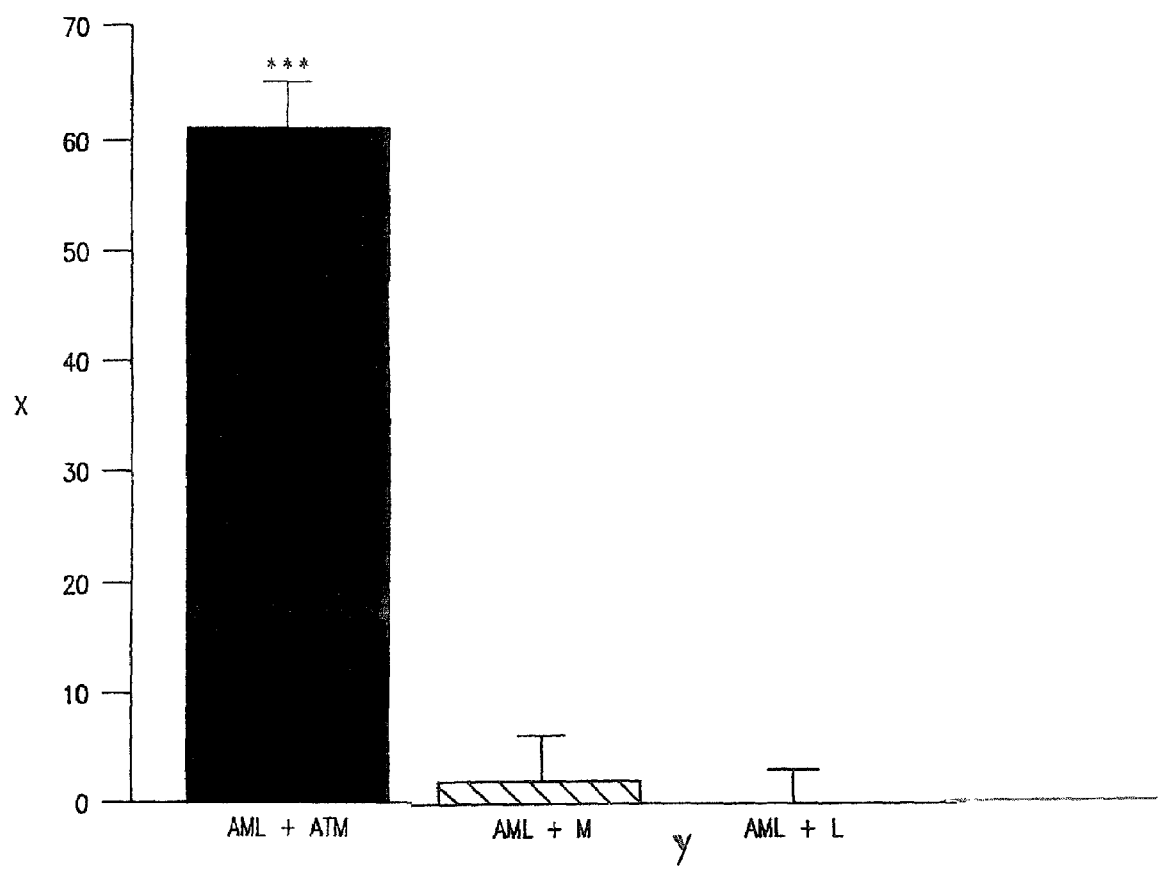
FIG. 5 shows the comparative effects of AML antioxidant activity when combined with different HMG-CoA reductase inhibitors at the same concentration. x is percent inhibition of lipid peroxidation and y is treatment with the combination of amlodipine and atorvastatin metabolite (AML+ATM), darkened panel; amlodipine and mevastatin (AML+M), cross-hatched panel; or amlodipine and lovastatin (AML+L), no lipid peroxidation inhibition; all at 1.0 μM. Values are mean±standard deviation for n=6 to 12. *** indicates $p<0.001$ versus control and other treatments.

The increased polarity of ATM, mediated by its additional hydroxy group, may facilitate stronger interactions with the formally charged AML, leading to distinct interactions with phospholipid molecules, as evidenced by x-ray diffraction analysis. The additional hydroxy group associated with the ATM also provides an additional abstractable proton that can be donated to free radical molecules (FIG. 4). Following the loss of the proton, the remaining unpaired free electron can be effectively stabilized in resonance structures of the metabolite, as shown in FIG. 4. The distinct antioxidant activity of the combination of AML with ATM is indicated by the observation that a similar effect could not be reproduced when AML was combined with each of two other statins (mevastatin and lovastatin), as demonstrated in FIG. 5. The results of in vivo investigations have indicated an important role for lipophilic antioxidants in reducing cardiovascular morbidity and mortality, especially CAD. LDL particles that have greater resistance to oxidative damage exhibit reduced cytotoxicity, interfere less with endothelium-derived nitric oxide production, and do not contribute to foam cell formation (Diaz M N, Frei B, Vita J A, Keaney J F. Antioxidants and atherosclerotic heart disease. *N. Engl. J. Med.* 1997; 337:408–416). Supplementation with an antioxidant has been shown to increase LDL resistance to oxidative modification and reduce endothelial cell cytotoxicity (Belcher J D, Balla J, Balla G, et al. Vitamin E, LDL, and endothelium. Brief oral vitamin supplementation prevents oxidized LDL-mediated vascular injury in vitro. *Arterioscler. Thromb.* 1993; 13:1779–1789). Probucol, a lipophilic antioxidant, attenuated the formation of atherosclerotic plaques in cholesterol-fed primates, an effect that correlated with increased resistance of LDL to oxidative damage (Sasahara M, Raines E W, Chait A, et al. Inhibition of hypercholesterolemia-induced atherosclerosis in the non-human primate by probucol. I. Is the extent of atherosclerosis related to resistance of LDL to oxidation? *J. Clin. Invest.* 1994; 94:155–164). This antioxidant inhibited the formation of lesions in Watanabe hereditary hyperlipidemic (WHHL) rabbits, a well-characterized animal model of atherosclerosis, independent of cholesterol-lowering effects (Carew T E, Schwenke D C, Steinberg D. Antiatherogenic effect of probucol unrelated to its hypocholesterolemic effect: Evidence that antioxidants in vivo can selectively inhibit low density lipoprotein degradation in macrophage-rich fatty streaks and slow the progression of atherosclerosis in the Watanabe heritable hyperlipidemic rabbit. *Proc. Natl. Acad. Sci. USA* 1987; 84:7725–7729). Beyond these animal studies, a placebo-controlled clinical study demonstrated that probucol reduced restenosis by 47% in patients with CAD following coronary-artery balloon angioplasty, presumably due to its antioxidant effects (Tardif J C, Cote G, Lesperance J, et al. Probucol and multivitamins in the prevention of restonosis after coronary angioplasty. Multivitamins and Probucol Study Group. *N Engl. J. Med.* 1997; 337:365–372). In a separate study, it was demonstrated that probucol, unlike antioxidant vitamins, had a beneficial effect on vascular remodeling in patients that had underwent angioplasty, as determined by intravascular ultrasound techniques (Cote G, Tardif J-C, Lesperance J, et al. Effects of probucol on vascular remodeling after coronary angioplasty. *Circulation* 1999; 99:30–35).

Thus, a review of the available data provides a mechanistic rationale for the use of lipophilic antioxidants to interfere with inflammatory processes associated with CAD.

By increasing the resistance of LDL and vascular cell membranes to oxidative damage, agents with antioxidant activity may effectively interfere with pathologic alterations in the vessel wall during atherogenesis. These processes include, but are not limited to, foam cell formation, endothelial dysfunction and toxicity, leukocyte and platelet adhesion, and arterial vasospasm, secondary to a loss of normal nitric oxide production. These cellular observations support epidemiologic analyses that indicate an inverse association between the serum levels of certain antioxidants and adverse outcomes associated with coronary disease (Stampfer M J, Hennekens C H, Manson J E, Colditz G A, Rosner B, Willett W C. Vitamin E consumption and the risk of coronary disease in women. *N. Engl. J. Med* 1993; 328:1450–1456; Rimm E B, Stampfer M J, Ascherio A, Giovannucci E, Colditz G A, Willett W C. Vitamin E consumption and the risk of coronary heart disease in men. *N Engl. J. Med.* 1993; 328:1450–1456; Enstrom J E, Kanim L E, Klein M A. Vitamin C intake and mortality among a sample of the United States population. *Epidemiology* 1992; 3:194–202; Riemersma R A, Wood D A, Macintyre C C, Elton R, Gey K F, Oliver M F. Low plasma vitamins E and C. Increased risk of angina in Scottish men. *Ann. N Y. Acad Sci.* 1989; 570:291–295; Ramirez J, Flowers N C. Leukocyte ascorbic acid and its relationship to coronary artery disease in man. *Am. J. Clin. Nutr.* 1980; 33:2079–2087; Hennekens C H, Buring J E, Manson J E, et al. Lack of effect of long-term supplementation with beta carotene on the incidence of malignant neoplasms and cardiovascular disease. *N. Engl. J. Med* 1996; 334:1145–1149; Losonczy K G, Harris T B, Havlik R J. Vitamin E and vitamin C supplement use and risk of all-cause and coronary heart disease mortality in older persons: The Established Populations for Epidemiologic Studies of the Elderly. *Am. J. Clin. Nutr.* 1996; 64:190–196). Several of these epidemiologic studies showed benefit with vitamin E, an antioxidant with limited capacity to interfere with oxidative modification. The results of this study would predict that the combination of AML and ATM would be significantly more effective than vitamin E in reducing vascular injury associated with CAD.

Figure 6A:
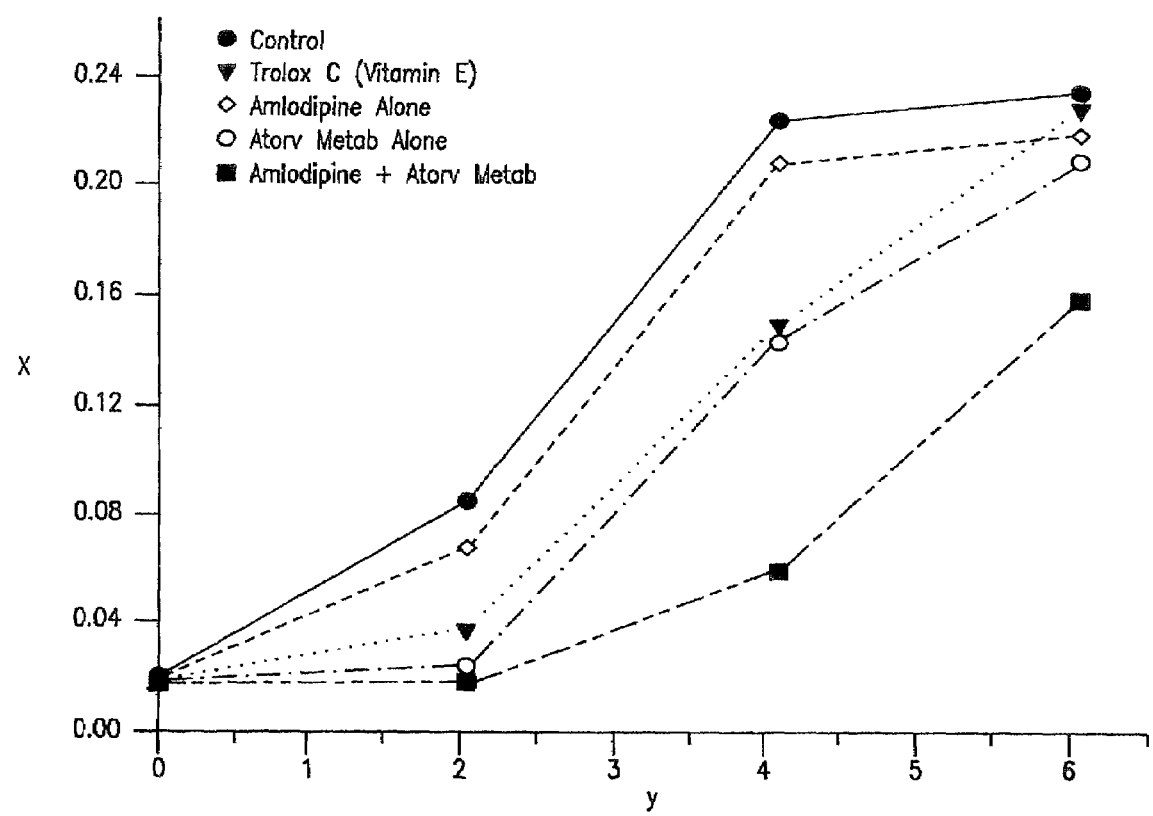
FIGS. 6A–6B show the synergistic antioxidant effects of AML and ATM in human LDL samples, as compared to Trolox C (soluble vitamin E). In (FIG. 6A), x is thiobarbituric reactive substances (TBARS) formation measured at an absorbance of 532 nm and y is time in hours. The control is indicated by filled circles with solid lines, Trolox C (soluble vitamin E) is indicated by filled, inverted triangles with small dashed lines, AML alone is indicated by open diamonds with long dashed lines, ATM alone is indicated by open circles with alternating long and short dashed lines, and AML and ATM is indicated by filled squares with dotted lines. In (FIG. 6B), x is thiobarbituric reactive substances (TBARS) formation measured at an absorbance of 532 nm and y is treatment with the combination of amlodipine (AML), darkened panel; atorvastatin metabolite (ATM), cross-hatched panel; or amlodipine and atorvastatin metabolite (AML+ATM), darkened panel, at a concentration of 3.0 μM. Values are mean±standard deviation. *** indicates $p<0.001$ versus control and other treatments.
Figure 6B:
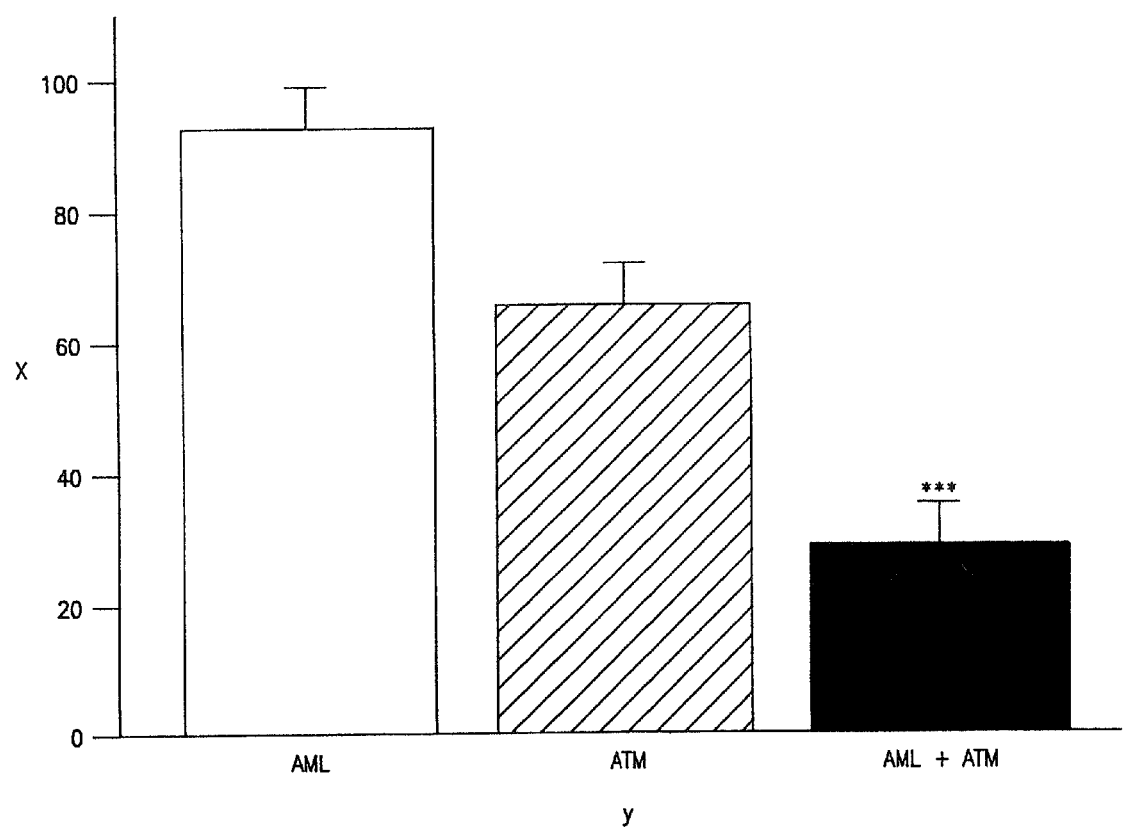

Synergistic Antioxidant Effects of Amlodipine with the Hydroxy Atorvastatin Metabolite in Human LDL:

The separate and combined antioxidant effects of AML and ATM were also evaluated in human LDL preparations. The ability of these agents to inhibit LDL peroxidation was assessed in vitro following addition of copper (10.0 μM) by measuring the levels of thiobarbituric reactive substances (TBARS), a marker of lipid peroxidation. FIG. 6 shows that the rate of LDL oxidation was characterized by sigmoidal curve kinetics with an initial lag phase followed by a sharp propagation and final plateau phase (Esterbauer H, Gebicki J, Puhl H, Jurgens G. The role of lipid peroxidation and antioxidants in oxidative modification of LDL. *Free Radic. Biol. Med.* 1992; 13:341–390). After a 4 h incubation period, the differential effects of these compounds could be clearly observed at a concentration of 3.0 μM. As compared to control lipid peroxidation (100% TBARS formation), TBARS formation for AML and ATM were 93.3±6% and 65.6±7%, respectively. When combined, however, TBARS formation was only 29.3±6%, levels that were significantly (p<0.01) lower than that observed for either drug alone. The synergistic antioxidant effect of the combination persisted at the 6 h time point. These findings provide further evidence for synergistic activity consistent with that observed in membrane vesicles, as the drug combination produced a level of inhibition that substantially exceeded their expected additive effect. The antioxidant activity of vitamin E was similar to that observed for ATM alone in these experiments.

Chemical Mechanisms for the Synergistic Activity of Amlodipine and Atorvastatin Metabolite:

The synergistic antioxidant activity observed for this drug combination in LDL and reconstituted lipid membranes suggests that these compounds interact directly with each other to scavenge lipid radicals. Based on thermodynamic considerations (FIG. 7), it is proposed that ATM reacts more quickly with lipid radicals (equation 1) than does AML, as described in equation 2. If these are the only two pathways available for these drugs when added together to the system, then their combined effect would only be additive. However, the combination of both compounds provides the possibility for a third pathway (equation 3), an alternative that is supported by the results of the peroxidation experiments in both LDL and lipid membranes. The combination of pathways 1 and 3 would produce a synergistic effect as it occurs more rapidly than pathway 2. Indeed, semi-empirical calculations suggest that reaction 3 is a favorable, exothermic process ($H_f$=−40.7 kJ/mol). Thus, the presence of the fast inhibitor (ATM) enables the slower inhibitor (AML) to remove free radicals more rapidly than if reacting with the lipid radicals on its own. The three pathways describing these interactions are as follows, in which LOO. represents a lipid radical:

(1) LOO• + ATM → LOOH + ATM• FAST
(2) LOO• + AML → LOOH + AML• SLOW
(3) ATM• + AML → ATM + AML• FAST

As a result of this synergy between AML and ATM, the recycled metabolite is now available for additional scavenging of lipid radicals. Overall, differences in the rates of inhibition between AML and ATM are based, in part, on the calculated enthalpies for these compounds and their respective radicals (FIG. 7). The smaller (i.e., more negative) the $H_f$ value, the more favorable is hydrogen abstraction associated with radical formation. Once formed, the unpaired radical associated with radical species can be stabilized in resonance structures.

Molecular Membrane Interactions of Amlodipine and Atorvastatin Metabolite:

Small-angle x-ray diffraction approaches were used to examine the molecular membrane interactions of the AML and ATM combination. This highly quantitative technique provides direct information on the structure of the membrane lipid bilayer in the absence and presence of the drugs. It has been previously reported that AML has high affinity for membrane lipids ($K_p$>10$^3$) under atherosclerotic conditions, as compared to other CCBs (Mason R P, Moisey D M, Shajenko L. Cholesterol alters the binding of $Ca^{2+}$ channel blockers to the membrane lipid bilayer. *Mol Pharmacol.* 1992; 41:315–321). The distinct lipophilicity of AML is attributed to its amphiphilic chemical structure that directs the molecule to an advantageous location in the membrane where it can then interfere with the propagation of free radicals by both biophysical and biochemical mechanisms, as previously described in detail by my laboratory (Mason R P, Leeds P R, Jacob R F, et al. Inhibition of excessive neuronal apoptosis by the calcium antagonist amlodipine and antioxidants in cerebellar granule cells. *J. Neurochem.* 1999; 72:1448–1456; Mason R P, Moisey D M, Shajenko L. Cholesterol alters the binding of $Ca^{2+}$ channel blockers to the membrane lipid bilayer. *Mol Pharmacol.* 1992; 41:315–321; Mason R P, Campbell S F, Wang S D, Herbette L G. Comparison of location and binding for the positively charged 1,4-dihydropyridine calcium channel antagonist amlodipine with uncharged drugs of this class in cardiac membranes. *Mol. Pharmacol.* 1989; 36:634–640; Mason R P, Walter M F, Trumbore M W, Olmstead Jr. E G, Mason P E. Membrane antioxidant effects of the charged dihydropyridine calcium antagonist amlodipine. *J. Mol. Cell. Cardiol.* 1999; 31:275–281) In membranes that are not enriched with cholesterol, amlodipine inhibited lipid peroxidation in a manner that could not be reproduced by other CCBs or the angiotensin converting enzyme (ACE)-inhibitor, captopril (Mason R P, Walter M F, Trumbore M W, Olmstead Jr. E G, Mason P E. Membrane antioxidant effects of the charged dihydropyridine calcium antagonist amlodipine. *J. Mol. Cell. Cardiol.* 1999; 31:275–281). In the same way, the chemical structure of the atorvastatin metabolite has amphiphilic properties that would enable the drug to interact strongly with the membrane lipid bilayer, as recently reported by my laboratory (Mason R P. Inhibition of oxidative damage to low density lipoproteins and isolated membranes by atorvastatin and its active metabolite. *J. Am. Coll. Cardiol.* 2000; 35:317A).

Figure 8A:
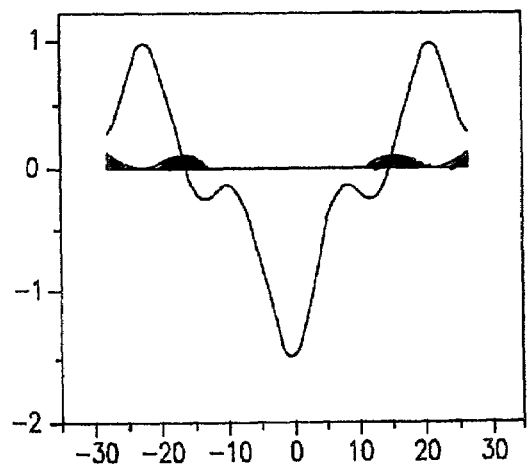
FIGS. 8A–8C show x-ray diffraction determination of the separate versus combined lipid membrane interactions of AML and ATM. x is relative electron density and y is angstroms from the middle of the lipid bilayer. In all three panels the control is the solid line.
Figure 8B:
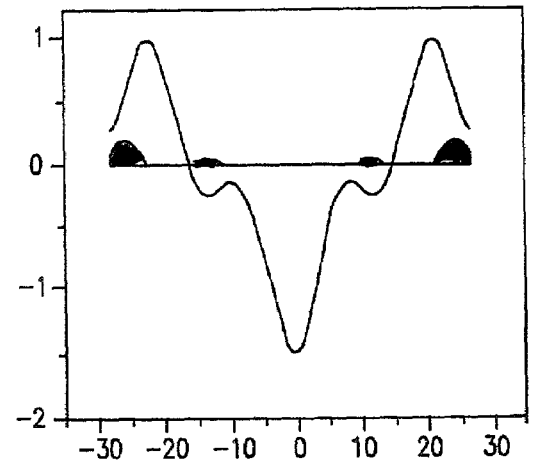
Figure 8C:
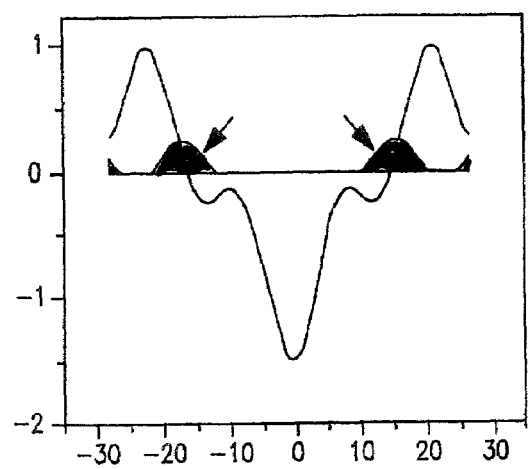
Figure 9:
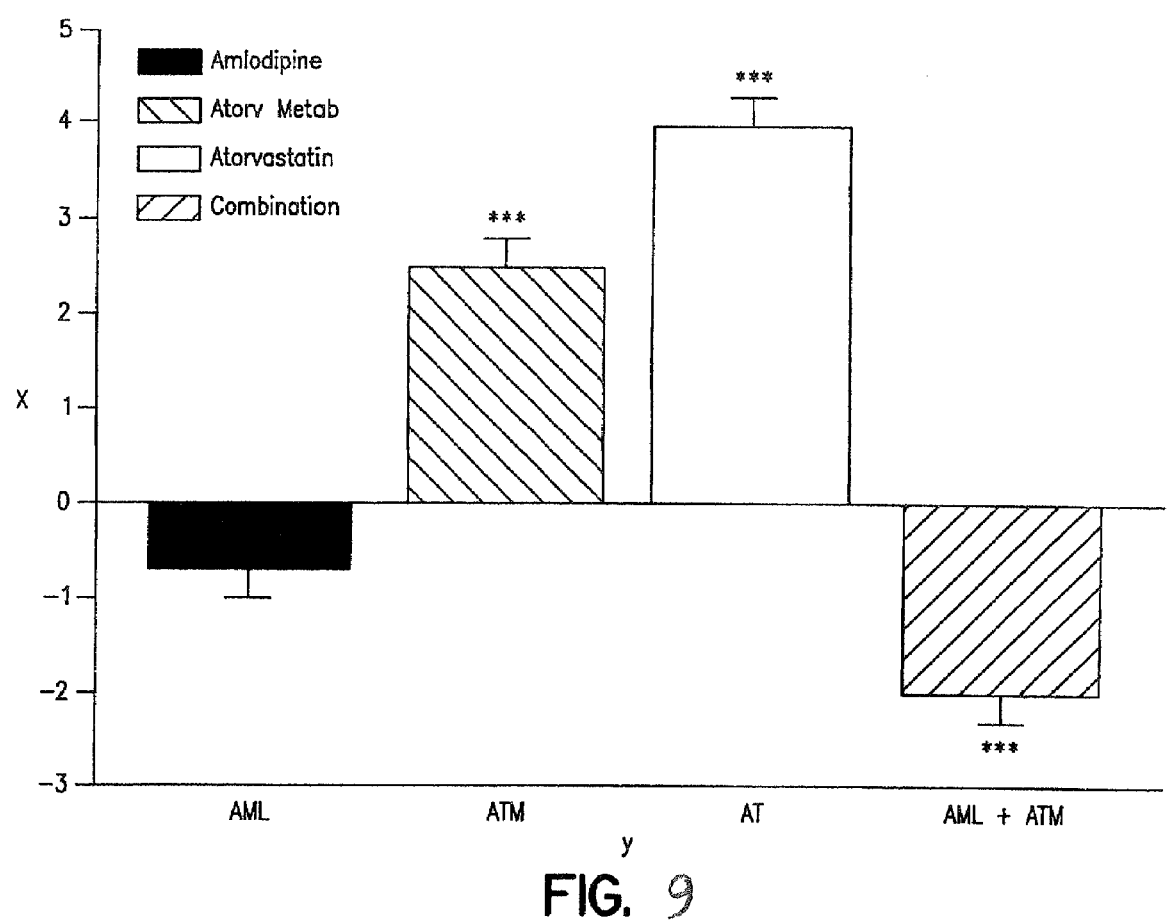
FIG. 9 shows the separate versus combined effects of AML and ATM on membrane bilayer dimensions as determined by x-ray diffraction analysis. x is the change in membrane width in angstroms and y is the treatment with AML, darkened panel; ATM, cross-hatched panel; and the combination of AML and ATM, hatched panel. Values are mean±standard deviation. *** indicates p<0.001 versus control and other treatments.

For these studies, the combination of AML and ATM were added to membrane vesicles reconstituted from cholesterol and phospholipid at a 0.5:1 mole ratio (FIG. 8). X-ray diffraction analysis of the membrane samples produced strong and reproducible diffraction patterns for representative control and drug-containing samples. In the absence of drug, the overall membrane bilayer width, including surface hydration, was 55.5 Å with an intrabilayer headgroup separation of 44 Å. The addition of the two drugs together at a ratio of drug to phospholipid of 1:15 produced distinct changes in the structure and organization of the phospholipid bilayer, as compared to the drugs added separately (FIG. 8). In the presence of the drug combination, the overall membrane bilayer width, including surface hydration, was reduced to 53.5 Å with an intrabilayer headgroup separation of 41 Å. Separately, the membrane bilayer widths of membranes containing AML and ATM alone were 54.8 Å and 58.0 Å, respectively (FIG. 9). These structural findings provide direct evidence that the combination of these agents differentially modulate the structure of lipid molecules, as compared to their separate effects.

Direct subtraction of the membrane electron density profiles (Å versus electrons/Å$^3$) demonstrated large differences in lipid structure that could be attributed to the presence of the drugs (FIG. 8). Specifically, the addition of the drug combination produced a broad increase in electron density associated with the upper hydrocarbon core/hydrated headgroup region of the membrane bilayer±11–21 Å from the center of the bilayer. This large increase in electron density distributed over 10 Å is attributed to the equilibrium location of the drugs in the membrane. Concomitant with this change was an observed disordering effect associated with the central hydrocarbon core region of the membrane, ±0–11 Å. This decrease in electron density is due to an increase in molecular volume resulting from the insertion of the drug molecules into a region of high molecular density near the membrane hydrocarbon core/water interface. Thus, it can be concluded from these data that the insertion of the drug combination into the membrane bilayer alters the intermolecular packing constraints of the phospholipid molecules in a manner similar to that observed with either reducing cholesterol content or increasing sample temperature (Tulenko T N, Chen M, Mason P E, Mason R P. Physical effects of cholesterol on arterial smooth muscle membranes: Evidence of immiscible cholesterol domains and alterations in bilayer width during atherogenesis. *J. Lipid Res.* 1998; 39:947–956; Chang H M, Reitstetter R, Mason R P, Gruener R. Attenuation of channel kinetics and conductance by cholesterol: An interpretation using structural stress as a unifying concept. *J. Member. Biol.* 1995; 143:51–63). Such changes in biophysical properties have been shown to interfere with the propagation of free radicals though the lipid bilayer matrix (McLean L R, Hagaman K A. Effect of lipid physical state on the rate of peroxidation of liposomes. *Free Radic. Biol. Med.* 1992; 12:113–119). Separately, AML and ATM effected distinct changes in membrane structure, as compared to the drug combination, due to specific interactions with constituent phospholipid molecules (FIGS. 8 and 9). While the drug combination effected a 2 Å or 4% decrease (p<0.01) in overall membrane width, the ATM separately produced a 5% increase (p<0.01) in width (2.5 Å) while AML alone did not significantly alter membrane dimensions, including the intrabilayer headgroup separation. As compared to AML alone, ATM produced a larger reduction in hydrocarbon core electron density. This effect on membrane structure may contribute to its greater antioxidant potency, as compared to AML. The combination of AML and ATM effected a new site of interaction with the membrane lipid bilayer, in addition to their separate locations in the membrane (FIG. 8).

Therefore, this invention is drawn to a pharmaceutical composition comprising amlodipine and atorvastatin metabolite. These individual pharmaceutical agents can be formulated in combination, or separately, in salts, forms, and dosages that produce maximal therapeutic responses. This combination therapy is designed to treat the various pathophysiological manifestations of arterial and related heart disease, including, but not limited to, hypertension, hyperlipidemia, atherosclerosis, arteriosclerosis, coronary artery disease, myocardial infarction, congestive heart failure, stroke, and angina pectoris. Specifically, this combination therapy will be designed to lower blood pressure and systemic lipid concentrations as well as the related pathophysiological results of the lack of their regulation, including, but not limited to, arterial weakening and plaque deposition. The effects of these individual agents on these various processes and events related to arterial and related heart disease, when used in combination can be additive and/or synergistic.

It will now be apparent to those skilled in the art that other embodiments, improvements, details, and uses can be made that are consistent with the letter and spirit of the foregoing disclosure and within the scope of this patent and the appended claims.

Experimental Methods

Dilinoleoyl phosphatidylcholine (DLPC), 1-palmitoyl-2-oleoyl phosphatidylcholine (POPC) and unesterified cholesterol were obtained from Avanti Polar Lipids Inc. (Alabaster, Ala.) and stored at −80° C. Aliquots of LDL (L-2139) from human plasma were obtained from Sigma Chemical Co. (St. Louis, Mo.). Sephadex G-25 M (PD-10) columns were purchased from Pharmacia Biotech Inc. (Piscataway, N.J.). Amlodipine besylate was obtained from Pfizer Central Research (Groton, Conn.) while the hydroxy metabolite of atorvastatin was provided by Parke Davis (Ann Arbor, Mich.). The ortho-hydroxy metabolite of atorvastatin was used in the experiments. Vitamin E, Trolox (a vitamin E analog), lovastatin, and mevastatin were purchased from Sigma Chemical Co. (St. Louis, Mo.).

Membrane Lipid Peroxidation Analysis:

The separate and combined dose-dependent antioxidant activities of these agents were examined in membranes enriched with PUFA prepared at a 0.5 cholesterol to phospholipid mole ratio (Mason R P, Walter M F, Trumbore M W, Olmstead Jr. E G, Mason P E. Membrane antioxidant effects of the charged dihydropyridine calcium antagonist amlodipine. *J. Mol Cell. Cardiol.* 1999; 31:275–281). The lipid (dilinoleoyl phosphatidylcholine and cholesterol) used for these samples was dissolved in HPLC-grade chloroform (25.0 mg/ml). An aliquot of the lipids (1.0 mg) was added to individual glass 13×100-mm test tubes and chloroform was removed by shell-drying under a steady stream of $N_2$ gas. The lipids were dried down in the absence or presence of drug(s) dissolved in ethanol. Residual solvent was removed under vacuum while the samples were shielded from light. Membrane vesicles were produced by rapidly mixing the dried lipids at room temperature following addition of 1.0 ml HEPES buffered saline (0.5 mM HEPES and 154.0 mM NaCl, pH, 7.2). The final phospholipid concentration was 1.0 mg/ml buffer and the final concentration of drug ranged from 10.0 nM through 10.0 μM.

Membrane lipid peroxidation was carried out at 37° C. in a shaking water bath without the addition of exogenous stimulants, as previously described in detail (Mason R P, Walter M F, Trumbore M W, Olmstead Jr. E G, Mason P E. Membrane antioxidant effects of the charged dihydropyridine calcium antagonist amlodipine. *J. Mol. Cell. Cardiol.* 1999; 31:275–281). At various time intervals (24, 48, 65, 72 h), an aliquot of lipid sample (10 to 100 μl) was removed before 25 μl of 5.0 mM ethylenediaminetetracetic acid (EDTA) and 20 μl of 35.0 mM butylated hydroxytoluene (BHT) was immediately added to the sample to stop the peroxidation reaction. The extent of membrane lipid peroxidation was measured by the CHOD-Iodide assay as previously described in detail (El-Saadani M, Esterbauer H, el-Sayed M, Goher M, Nassar A Y, Jurgens G. A spectrophotometric assay for lipid peroxides in serum lipoproteins using a commercially available reagent. *J. Lipid. Res.* 1989; 30:627–630). The quantity of $I_3^-$ was measured from the following reaction in which L represents a phospholipid molecule:

$$LOOH+2H^++2I^-\rightarrow LOH+H_2O+I_2$$

$$I_2+I^-\rightarrow I_3^-$$

An aliquot of the membrane sample was removed at various time points and then added to 1.0 ml of CHOD color reagent (E. M. Science, Gibbstown, N.J.) that includes 20.0 μM BHT, 24.0 &M EDTA, and 0.2% Triton-X. The sample was then covered with foil and allowed to incubate for 2 h in the absence of light before measuring the absorbance of the sample at 365 nm ($\epsilon=2.4\times10^4$ $M^{-1}$ $cm^{-1}$). The background sample was run along the test samples in triplicate and contains 76.7 &l of 0.652 mM HEPES, 20 μl of 5.0 mM EDTA and 3.3 μl of DDI water. The extent of lipid peroxidation was measured in triplicate for each drug concentration and compared to control samples that did not contain drug. The statistical significance of these experiments was assessed by the non-paired t-test. Significance was accepted at p<0.05. final phospholipid concentration was 1.0 mg/ml buffer and the final concentration of drug ranged from 10.0 nM through 10.0 μM.

Membrane lipid peroxidation was carried out at 37° C. in a shaking water bath without the addition of exogenous stimulants, as previously described in detail (Mason R P, Walter M F, Trumbore M W, Olmstead Jr. E G, Mason P E. Membrane antioxidant effects of the charged dihydropyridine calcium antagonist amlodipine. *J Mol. Cell. Cardiol.* 1999; 31:275–281). At various time intervals (24, 48, 65, 72 h), an aliquot of lipid sample (10 to 100 μl) was removed before 25 μl of 5.0 mM ethylenediaminetetracetic acid (EDTA) and 20 μl of 35.0 mM butylated hydroxytoluene (BHT) was immediately added to the sample to stop the peroxidation reaction. The extent of membrane lipid peroxidation was measured by the CHOD-Iodide assay as previously described in detail (El-Saadani M, Esterbauer H, el-Sayed M, Goher M, Nassar A Y, Jurgens G. A spectrophotometric assay for lipid peroxides in serum lipoproteins using a commercially available reagent. *J. Lipid. Res.* 1989; 30:627–630). The quantity of $I_3^-$ was measured from the following reaction in which L represents a phospholipid molecule:

$$LOOH+2H^++2I^-\rightarrow LOH+H_2O+I_2$$

$$I_2+I^-\rightarrow I_3^-$$

An aliquot of the membrane sample was removed at various time points and then added to 1.0 ml of CHOD color reagent (E.M. Science, Gibbstown, N.J.) that includes 20.0 μM BHT, 24.0 &M EDTA, and 0.2% Triton-X. The sample was then covered with foil and allowed to incubate for 2 h in the absence of light before measuring the absorbance of the sample at 365 nm ($\epsilon=2.4\times10^4$ $M^{-1}$ $cm^{-1}$). The background sample was run along the test samples in triplicate and contains 76.7 &l of 0.652 mM HEPES, 20 μl of 5.0 mM EDTA and 3.3 μl of DDI water. The extent of lipid peroxidation was measured in triplicate for each drug concentration and compared to control samples that did not contain drug. The statistical significance of these experiments was assessed by the non-paired t-test. Significance was accepted at p<0.05.

LDL Oxidation Determination:
In addition to lipid membranes, the antioxidant

LDL Oxidation Determination:
In addition to lipid membranes, the antioxidant activity of AML and ATM was evaluated in human LDL. The EDTA content of the LDL samples obtained from human plasma was removed by gel filtration with PD-10 Sephadex G25-M filtration columns; PBS (nitrogen purged) was used as the eluent. The LDL samples (50 μg of protein/mL) were then preincubated with or without drug (3.0 μM) for 30 mm at 37° C. Oxidation of LDL was then induced by the addition of 10.0 μM $CuSO_4$. The time course of LDL oxidation, measured by TBARS formation, was followed for 6 h at 37° C. (Mak I T, Kramer J H, Weglicki W B. Potentiation of free radical-induced lipid peroxidative injury to sarcolemmal membranes by lipid amphiphiles. *J. Biol. Chem.* 1986; 261:1153–1157). LDL oxidation, as determined by the TBARS methods, followed sigmoidal curve kinetics with an initial lag phase followed by a sharp propagation and final plateau phase (Esterbauer H, Gebicki J, Puhl H, Jurgens G. The role of lipid peroxidation and antioxidants in oxidative modification of LDL. *Free Radic. Biol. Med.* 1992; 13:341–390). The protein content of the LDL was determined using the Coomassie Protein Plus assay kit from Pierce Chemical. A rapid and sensitive method for the quantitation of microgram quantities of protein utilizing the principle of protein-dye binding. *Anal. Biochem.* 1976; 72:248–254).

Small Angle X-ray Diffraction Analysis:
Small-angle X-ray diffraction analyses were used to directly examine the molecular membrane interactions of AML, and ATM. The lipids (1-palmitoyl-2-oleoyl phosphatidylcholine and cholesterol) used for these samples were dissolved in HPLC-grade chloroform (10.0 mg/ml). Membrane vesicles were produced from these lipids by the same method as described for the peroxidation experiments. The final phospholipid concentration was 5.0 mg/ml buffer and the mole ratio of drug to phospholipid was 1:15. Membrane samples were oriented for diffraction analysis by subjecting them to centrifugation as previously described (Chester D W, Herbette L G, Mason R P, Joslyn A F, Triggle D J, Koppel D E. Diffusion of dihydropyridine calcium channel antagonists in cardiac sarcolemmal lipid multibilayers. *Biophys. J.* 1987; 52:1021–1030). Briefly, vesicles were placed in sedimentation cells that contained an aluminum foil substrate. The vesicles were sedimented in an SW-28 rotor (Beckman Instruments Fullerton, Calif.) at 35,000×g for 1.5 h at 5° C. Following centrifugation, the supernatant was removed from the pellets and the samples were then mounted on to curved glass supports. Samples were placed in sealed canisters to control relative humidity and temperature during the diffraction experiments, as previously described in detail (Chester D W, Herbette L G, Mason R P, Joslyn A F, Triggle D J, Koppel D E. Diffusion of dihydropyridine calcium channel antagonists in cardiac sarcolemmal lipid multibilayers. *Biophys. J.* 1987; 52: 1021–1030).

X-ray diffraction experiments were conducted by aligning the samples at grazing incidence with respect to a collimated, nickel-filtered monochromatic X-ray source ($CuK_\alpha$ 1.54 Å) produced by a high-brilliance rotating anode microfocus generator (Rigaku Rotaflex RU-200, Danvers, Mass.). The fixed geometry beam line consisted of a single, nickel-coated Franks mirror to define a line source where $K_\alpha$ and $K_\alpha$ are unresolved. The diffraction data were collected on a one-dimensional, position-sensitive electronic detector (Innovative Technologies, Newburyport, Mass.) placed at a distance of 150 mm from the sample. Each meridional diffraction peak was Lorentz and background corrected, as previously described (Mason R P, Gonye G E, Chester D W, Herbette L G. Partitioning and location of Bay K 8644, 1,4-dihydropyridine calcium channel agonist, in model and biological membranes. *Biophys. J.* 1989; 55:769–778). The phases for the four-order data were determined by swelling analysis (Moody M F. X-ray diffraction pattern of nerve myelin: A method for determining the phases. *Science* 1963; 142:1173–117). Fourier transformations of the data were generated from the diffraction data with Origin software (Microcal Software, Northampton, Mass.).

What is claimed is:

1. A pharmaceutical composition comprising:
an effective amount of amlodipine;
an effective amount of a substantially pure form of hydroxylated atorvastatin metabolite; and
a pharmaceutically acceptable carrier or diligent,
wherein said hydroxylated atorvastatin metabolite is selected from the group consisting of (2R-trans)-5-(4-fluorophenyl)-2-(1-methylethyl)-N-(4-hydroxyphenyl)-4-phenyl-1-[2-(tetrahydro-4-hydroxy-6-oxo-2H-pyran-2-yl)ethyl]-1H-pyrrole-3-carboxamide, (2R -trans)-5-(4-fluorophenyl)-2-(1-methylethyl)-N-(3-hydroxyphenyl)-4-phenyl-1-[-(tetrahydro-4-hydroxy-6-oxo-2H-pyran-2-yl)ethyl]-1H-pyrrole-3-carboxamide, and (2R -trans)-5-(4-fluorophenyl)-2-(1-methylethyl)-N-(2-hydroxyphenyl)-4-phenyl-1-[2-(tetrahydro-4-hydroxy-6-oxo-2H-pyran-2-yl)ethyl]-1H-pyrrole-3-carboxamide, and wherein the effective amounts of amlodipine and hydroxylated atorvastatin metabolite synergistically inhibit lipid peroxidation in human low density lipoprotein or lipid membrane to achieve a therapeutic effect.

2. The pharmaceutical composition of claim 1 wherein said amlodipine comprises amlodipine besylate.

3. The pharmaceutical composition of claim 1 wherein said amounts of amlodipine and hydroxylated atorvastatin metabolite are coordinated to synergistically inhibit lipid peroxidation to the extent necessary to achieve the therapeutic effect of reducing the risk of arterial and related heart disease.

4. The pharmaceutical composition of claim 3 wherein said arterial and related heart disease is selected from the group consisting of hypertension, hyperlipidemia, atherosclerosis, arteriosclerosis, coronary artery disease, myocardial infarction, congestive heart failure, stroke, and angina pectoris.

5. The pharmaceutical composition of claim 1 wherein said amounts of amlodipine and hydroxylated atorvastatin metabolite are coordinated to synergistically inhibit lipid peroxidation.

6. A pharmaceutical composition comprising:
an effective amount of amlodipine;
an effective amount of a substantially pure form of hydroxylated atorvastatin metabolite; and
a pharmaceutically acceptable carrier or diligent;
wherein said hydroxylated atorvastatin metabolite is selected from the group consisting of (2R-trans)-5-(4-fluorophenyl)-2-(1-methylethyl)-N-(4-hydroxyphenyl)-4-phenyl-1-[2-(tetrahydro-4-hydroxy-6-oxo-2H-pyran-2-yl)ethyl]-1H-pyrrole-3-carboxamide, (2R -trans)-5-(4-fluorophenyl)-2-(1-methylethyl)-N-(3-hydroxyphenyl)-4-phenyl-1-[2-(tetrahydro-4-hydroxy-6-oxo-2H-pyran-2-yl)ethyl]-1H-pyrrole-3-carboxamide, and (2R -trans)-5-(4-fluorophenyl)-2-(1-methylethyl)-N-(2-hydroxyphenyl)-4-phenyl-1-[2-(tetrahydro-4-hydroxy-6-oxo-2H-pyran-2-yl)ethyl]-1H-pyrrole-3-carboxamide, and wherein said effective amounts of amlodipine and hydroxylated atorvastatin metabolite are selected such that a synergistic antioxidant effect is achieved.

7. A pharmaceutical composition comprising:
an effective amount of amlodipine;
an effective amount of a substantially pure form of hydroxylated atorvastatin metabolite; and
a pharmaceutically acceptable carrier or diluent;
wherein said hydroxylated atorvastatin metabolite is selected from the group consisting of (2R-trans)-5-(4-fluorophenyl)-2-(1-methylethyl)-N-(4-hydroxyphenyl)-4-phenyl-1-[2-(tetrahydo-4-hydroxy-6-oxo-2H-pyran-2-yl)ethyl]-1-pyrrole-3-carboxamide, (2R trans)-5-(4-fluorophenyl)-2-(1-methylethyl)-N-(3-hydroxyphenyl)-4-phenyl-1-[2-(tetrahydro-4-hydroxy-6-oxo-2H-pyran-2-yl)ethyl]-1-pyrrole-3-carboxamide, and (2R trans)-5-(4-fluorophenyl)-2-(1-methylethyl)-N-(2-hydroxyphenyl)-4-phenyl-1-[2-(tetrahydro-4-hydroxy-6-oxo-2-yl)ethyl]-1H-pyrrole-3-carboxamide, and wherein said effective amounts of amlodipine and hydroxylated atorvastatin metabolite are selected such that a synergistic inhibition of lipid peroxidation is achieved.

8. The pharmaceutical composition of claim 7 wherein said selection is further coordinated for achieving a synergistic antioxidant effect.

9. The pharmaceutical composition of claim 6, wherein said composition is used to treat atherosclerosis.

10. The pharmaceutical composition of claim 9, wherein said atherosclerosis involves diseases selected from the group consisting of myocardial infarction, stroke, transient isehemic attack, coronary heart disease and a combination thereof.

11. The pharmaceutical composition of claim 6 further comprising an effective amount of a lipophilic antioxidant.

* * * * *

UNITED STATES PATENT AND TRADEMARK OFFICE
CERTIFICATE OF CORRECTION

PATENT NO.         : 7,129,265 B2
APPLICATION NO.    : 10/033149
DATED              : October 31, 2006
INVENTOR(S)        : R. Preston Mason It is certified that error appears in the above-identified patent and that said Letters Patent is hereby corrected as shown below:

In column 13, line 55 (claim 1) "carrier or diligent" should read -- carrier or diluent --

In column 13, line 62 (claim 1) "phenyl-1-[-tetrahydro-" should read -- phenyl-1-[2-tetrahydro- --

In column 14, line 27 (claim 6) "carrier or diligent" should read -- carrier or diluent --

In column 14, line 52 (claim 7) "1-pyrrole-3-carboxamide," should read
-- 1H-pyrrole-3-carboxamide, --

In column 14, line 54 (claim 7) "-pyran-2-yl)ethyl]-1-" should read -- -pyran-2-yl)ethyl]-1H- --

In column 14, line 57 (claim 7) "-6-oxo-2-yl)ethyl]-" should read -- -6-oxo-2H-pyran-2-yl)ethyl]- --

Signed and Sealed this

Sixth Day of April, 2010

David J. Kappos
*Director of the United States Patent and Trademark Office*